United States Patent
Garza

(10) Patent No.: US 9,987,015 B2
(45) Date of Patent: Jun. 5, 2018

(54) COVERED EMBOLIC COILS

(71) Applicant: INCUMEDx, Inc., Fremont, CA (US)

(72) Inventor: Armando Garza, San Jose, CA (US)

(73) Assignee: INCUMEDx, Inc., Fremont, CA (US)

( * ) Notice: Subject to any disclaimer, the term of this patent is extended or adjusted under 35 U.S.C. 154(b) by 388 days.

(21) Appl. No.: 14/808,550

(22) Filed: Jul. 24, 2015

(65) Prior Publication Data

US 2016/0022275 A1    Jan. 28, 2016

Related U.S. Application Data

(60) Provisional application No. 62/029,413, filed on Jul. 25, 2014.

(51) Int. Cl.
*A61M 29/00* (2006.01)
*A61F 2/06* (2013.01)
(Continued)

(52) U.S. Cl.
CPC ........ *A61B 17/12177* (2013.01); *A61B 17/12* (2013.01); *A61B 17/1214* (2013.01); *A61B 17/1215* (2013.01); *A61B 17/12031* (2013.01); *A61B 17/12113* (2013.01); *B23H 3/00* (2013.01); *B23K 11/002* (2013.01); *B23K 26/21* (2015.10); *B23K 26/361* (2015.10); *B23K 26/362* (2013.01); *C23F 1/00* (2013.01); *C23F 4/00* (2013.01); *C25F 3/14* (2013.01);
(Continued)

(58) Field of Classification Search
CPC .... A61B 17/12113; A61B 17/1214–17/12154; A61F 2/88; A61M 25/0012
USPC .................................. 606/191, 200
See application file for complete search history.

(56) References Cited

U.S. PATENT DOCUMENTS 3,687,129 A     8/1972  Nuwayser
4,553,545 A    11/1985  Maass et al.
(Continued)

FOREIGN PATENT DOCUMENTS

AU    2012202380 A1    5/2012
CN      102481436 A    5/2012
(Continued)

OTHER PUBLICATIONS

International Search Report and Written Opinion dated Oct. 7, 2015, for PCT Application PCT/US2015/042074, 16 pages.
(Continued)

*Primary Examiner* — Christopher L Templeton
*Assistant Examiner* — Majid Jamialahmadi
(74) *Attorney, Agent, or Firm* — Goodwin Procter LLP

(57) ABSTRACT

An embolic implant for treating aneurysms or other vascular disorders may include a cover component of unitary construction that is disposed about the exterior of a microcoil such that it does not extend into a lumen formed by the coil. The cover can enhance packing volume and density per unit length of coil, and can prevent blood flow and cause blood clotting while not risking rupture of the vascular disorder. The cover may also provide a platform for the application of multiple treatments and/or therapies including, for example, functionalized and/or bioactive coatings, drug coatings, gene therapy, thrombogenicity control coatings, and surface modifications, while preserving key coil performance attributes.

35 Claims, 13 Drawing Sheets

(51) Int. Cl.
  *A61B 17/00* (2006.01)
  *A61B 17/12* (2006.01)
  *B23K 26/21* (2014.01)
  *B23H 3/00* (2006.01)
  *B23K 11/00* (2006.01)
  *B23K 26/362* (2014.01)
  *C23F 1/00* (2006.01)
  *C23F 4/00* (2006.01)
  *C25F 3/14* (2006.01)
  *B23K 26/361* (2014.01)

(52) U.S. Cl.
  CPC ............ *A61B 2017/00526* (2013.01); *A61B 2017/00867* (2013.01); *A61B 2017/1205* (2013.01)

(56) References Cited

U.S. PATENT DOCUMENTS

| | | | |
|---|---|---|---|
| 5,064,435 | A | 11/1991 | Porter |
| 5,078,726 | A | 1/1992 | Kreamer |
| 5,151,105 | A | 9/1992 | Kwan-Gett |
| 5,226,911 | A | 7/1993 | Chee et al. |
| 5,382,259 | A * | 1/1995 | Phelps ............ A61B 17/12022 604/907 |
| 5,423,849 | A | 6/1995 | Engelson et al. |
| 5,582,619 | A | 12/1996 | Ken |
| 5,624,449 | A | 4/1997 | Pham et al. |
| 5,624,461 | A | 4/1997 | Mariant |
| 5,853,400 | A | 12/1998 | Samson |
| 5,941,888 | A | 8/1999 | Wallace et al. |
| 5,976,162 | A | 11/1999 | Doan et al. |
| 6,171,326 | B1 | 1/2001 | Ferrera et al. |
| 6,221,086 | B1 | 4/2001 | Forber |
| 6,530,934 | B1 | 3/2003 | Jacobsen et al. |
| 6,635,069 | B1 | 10/2003 | Teoh et al. |
| 6,663,650 | B2 | 12/2003 | Sepetka et al. |
| 6,705,323 | B1 | 3/2004 | Nikolchev et al. |
| 7,309,345 | B2 | 12/2007 | Wallace |
| 7,316,701 | B2 | 1/2008 | Ferrera et al. |
| 7,326,225 | B2 | 2/2008 | Ferrera et al. |
| 7,485,123 | B2 | 2/2009 | Porter |
| 7,879,064 | B2 | 2/2011 | Monstadt et al. |
| 8,066,036 | B2 | 11/2011 | Monetti et al. |
| 8,172,862 | B2 | 5/2012 | Wallace et al. |
| 8,308,751 | B2 | 11/2012 | Gerberding |
| 8,313,506 | B2 | 11/2012 | Davis et al. |
| 8,361,104 | B2 | 1/2013 | Jones et al. |
| 8,444,668 | B2 | 5/2013 | Jones et al. |
| 2002/0020417 | A1 * | 2/2002 | Nikolchev ....... A61B 17/12022 128/831 |
| 2004/0079429 | A1 | 4/2004 | Miller et al. |
| 2006/0058834 | A1 | 3/2006 | Do et al. |
| 2006/0100661 | A1 | 5/2006 | Jaeger et al. |
| 2006/0271086 | A1 | 11/2006 | Ramzipoor et al. |
| 2011/0245861 | A1 | 10/2011 | Chen et al. |
| 2013/0116722 | A1 | 5/2013 | Aboytes et al. |

FOREIGN PATENT DOCUMENTS

| | | |
|---|---|---|
| EP | 0617633 A1 | 10/1994 |
| EP | 0792623 A1 | 9/1997 |
| EP | 1078610 A2 | 2/2001 |
| EP | 1543849 A1 | 6/2005 |
| JP | 2000316980 A | 11/2000 |
| JP | 2013212374 A | 10/2013 |
| WO | WO-199409705 A1 | 5/1994 |
| WO | WO-1994011051 A1 | 5/1994 |
| WO | WO-1999009893 A1 | 3/1999 |
| WO | WO-2001067991 | 9/2001 |
| WO | WO-200074577 A9 | 5/2002 |
| WO | WO-2004010878 A1 | 2/2004 |
| WO | WO-2006034149 A2 | 3/2006 |
| WO | WO-20130184595 A1 | 12/2013 |

OTHER PUBLICATIONS

European Search Report issued for EP application No. 15745737.5, dated Feb. 9, 2018.

* cited by examiner

COVERED EMBOLIC COILS

CROSS-REFERENCE TO RELATED APPLICATION

This application claims priority to and the benefit of, and incorporates herein by reference in its entirety, U.S. Provisional Patent Application No. 62/029,413, which was filed on Jul. 25, 2014.

TECHNICAL FIELD

In general, various embodiments of this invention relate to embolic implants for use in the minimally-invasive treatment of aneurysms and other vascular disorders and, more specifically, to an embolic implant including a cover disposed about a microcoil that can achieve more effective and predictable outcomes during such treatment.

BACKGROUND

In general, an aneurysm is a swelling or bulge that forms a cavity in the wall of a blood vessel. One type of aneurysm is a cerebral aneurysm, which forms in an artery of the brain. A cerebral aneurysm may develop suddenly without initial symptoms, and can cause extreme pain. In general, in 15% of cerebral aneurysm cases, the patient dies suddenly upon development of the cerebral aneurysm; in another 15% of cerebral aneurysm cases, the patient dies under medical treatment; and in 30% of cerebral aneurysm cases, the patient survives after treatment but feels an acute aftereffect. As such, a cerebral aneurysm (or any aneurysm) is a very concerning development.

The treatment of aneurysms and other similar vascular disorders often involves the placement of microcoils within the cavity formed by the aneurysm or disorder. Doing so can cause blood to clot, prevent an additional inflow of blood, and decrease the risk of the aneurysm or disorder rupturing (i.e., an embolization). In order to be effective, an embolic microcoil must apply pressure sufficient to prevent additional blood flow, but not an excessive amount of pressure that causes rupture.

To improve their function, some existing coils include integrated, mesh-like embolic ribbon(s) that extend outwardly in a radial direction from a central support member. Under a cross-sectional view, looking along the longitudinal axis of the central support member, the mesh ribbon and support member are fixedly integrated and/or intersect one another. Such coil structures are typically manufactured using thin metal film. The film is often formed using vapor deposition techniques or by sputtering onto the support member, which is wound onto a core cylindrical mandrel. After the mandrel and support member have been coated with the thin metal film, the mesh pattern is cut using laser, mechanical, or conventional means. While such coils can offer an increased occlusive surface area, they also have a large cross-sectional profile that can create complications during delivery through a microcatheter. This structure may also result in the placement of excessive pressure on the aneurysm wall (thereby risking its rupture), inadequate stability, and/or inadequate biocompatibility with the interior of the aneurysm sac.

Other existing microcoils are overlaid with a fibrous braided cover component. Braided covers are typically formed from stiff metallic wires braided in an overlapping pattern. Like mesh ribbons, braided covers can enhance the ability of the coil to fill and occlude the aneurysm into which it is placed. However, a braided cover exhibits a number of drawbacks as well. The inherent wire-on-wire design creates a stiff configuration that can cause friction during delivery and excessive pressure upon deployment (potentially causing rupture). The wire-on-wire design can also cause undesirable mechanical and/or corrosive wear known as fretting. In addition, the relative motion between wires makes it difficult to incorporate surface treatment and/or therapy options into the cover.

Accordingly, needs exist for an improved microcoil covering that can disrupt blood flow while not risking rupture of the aneurysm. Further, a covering is needed that effectively enables the delivery of surface treatments and other therapies.

SUMMARY OF THE INVENTION

In various embodiments, the present invention relates to an embolic implant having a cover component that can prevent blood flow and cause blood clotting while not risking rupture of the vascular disorder. The cover may be disposed about the exterior of the coil such that it does not extend into a lumen formed by the coil. In certain embodiments, the cover is of unitary construction and may include through-thickness patterns (e.g., stent-like patterns) that enable greater packing volume and density per unit length of coil than existing devices, while preventing the exertion of excessive pressure on the aneurysm wall. In comparison to existing devices, the coil may exhibit a significant increase in biocompatible/blood-contacting surface area for effectively achieving stasis of blood-flow within the aneurysm sac. In some embodiments, the cover component provides a vehicle or platform for the application of multiple treatments and/or therapies including, for example, functionalized and/or bioactive coatings, drug coatings, gene therapy, thrombogenicity control coatings, and surface modifications (e.g., surface texture or roughness modifications, ion implantation, and surface charge alterations). The covered embolic coil can be used with known bare platinum coil (BPC) based techniques and instructions, for example, microcatheter based delivery and radiopacity/visualization, and in conjunction with certain known accessories.

In general, in one aspect, embodiments of the invention feature an implant adapted for use in treating a vascular disorder. The implant may include an embolic coil forming a lumen, and a cover of unitary construction disposed about an exterior of the embolic coil, where the cover does not extend into the lumen.

In various embodiments, the embolic coil includes a bare platinum coil. In some instances, the cover is expandable such that it covers the embolic coil in a constrained configuration during delivery of the implant to the vascular disorder and assumes an expanded configuration when the implant is placed within the vascular disorder. In some instances, the cover covers more surface area of the embolic coil in the expanded configuration than in the constrained configuration. The cover may be spaced apart from the embolic coil along at least a portion of the embolic coil when the cover is in the expanded configuration. In the expanded configuration of the cover, the implant may have a biocompatible blood-contacting surface area between 110% and 200% of the embolic coil alone.

In some cases, the cover includes a shape memory material. In some of the same or other cases, the cover includes a pattern, such as a through-thickness cut pattern (e.g., a stent-like pattern). The pattern may include cells, which can be closed cells, open cells, hybrid cells, or combinations thereof. In some instances, the cells are sized as a function of at least one of flow diversion, blood interaction, and expansion characteristics of the cover. In certain cases, the cells themselves can have a constrained configuration and an expanded configuration. In some instances, the cover includes at least one of a functionalized bioactive coating, a drug coating, a gene therapy coating, a thrombogenicity control coating, and surface modifications (e.g., surface texture alterations, surface roughness alterations, ion implantations, and surface charge alterations).

In some instances, the cover and embolic coil are concentric. In other instances, the cover and embolic coil are eccentric. The implant may include a packing volume in a range from 2 to 7 times a packing volume of the embolic coil alone. The embolic coil may be a framing coil, a filling coil, and/or a finishing coil.

The cover may include a biocompatible MRI-safe material. The cover may have a length of up to 50 cm, and may be helically wound. In some instances, the implant can include a second cover of unitary construction disposed about the exterior of the embolic coil, where the second cover does not extend into the lumen of the embolic coil.

In general, in another aspect, embodiments of the invention feature a method of delivering an implant to a vascular disorder. The method can include the step of advancing the implant, coupled to a delivery pusher, in proximity to the vascular disorder. The implant may include an embolic coil forming a lumen, and a cover of unitary construction disposed about an exterior of the embolic coil in a constrained configuration, where the cover does not extend into the lumen. The method can also include the step of releasing the implant from the delivery pusher and into the vascular disorder, whereby the cover expands into an expanded configuration.

In various embodiments, the vascular disorder is a cerebral aneurysm. In some instances, the cover covers more surface area of the embolic coil in the expanded configuration than in the constrained configuration. In the expanded configuration of the cover, the implant may include a biocompatible blood-contacting surface area between 110% and 200% of the embolic coil alone. The cover may be spaced apart from the embolic coil along at least a portion of the embolic coil when the cover is in the expanded configuration. In some cases, the cover includes a shape memory material. In some of the same or other cases, the cover includes a pattern, such as a through-thickness cut pattern.

In general, in yet another aspect, embodiments of the invention feature a method of manufacturing an implant for use in treating a vascular disorder. The method can include the steps of obtaining an embolic coil forming a lumen, forming a cover of unitary construction by creating a pattern in a sheet of unitary construction using a subtractive manufacturing technique, and disposing the cover about an exterior of the embolic coil, such that the cover does not extend into the lumen formed by the embolic coil.

In various embodiments, the sheet includes a metallic foil, made from, for example, nitinol, tantalum, tungsten, platinum, platinum iridium, cobalt chrome, magnesium, iron, stainless steel, or combinations and alloys thereof. In some instances, the sheet has a thickness in a range from about 5 microns to about 250 microns. The subtractive manufacturing technique can include a laser technique, a mechanical technique, a wet chemical technique, an electrochemical masking technique, a maskless electrochemical technique, etching, milling, photochemical machining, or photoelectrochemical machining.

In some cases, disposing the cover about the exterior of the embolic coil includes helically wrapping the cover about the exterior of the embolic coil. In other cases, disposing the cover about the exterior of the embolic coil includes shaping the cover into a tubular geometry (e.g., by heat setting) and placing the cover over the embolic coil.

In some instances, the method also includes the steps of disposing the cover and the embolic coil in a holding tube that maintains the cover in a constrained configuration about the exterior of the embolic coil, attaching the cover to the embolic coil at at least one end, and pushing the attached cover and embolic coil into a second tube that maintains the constrained configuration of the cover. In certain cases, attaching the cover to the embolic coil can include laser welding, resistance welding, applying a medical adhesive, applying continual coatings, and/or employing a mechanical interference fit. The method can also include the step of attaching the second tube to a delivery pusher.

These and other objects, along with advantages and features of the embodiments of the present invention herein disclosed, will become more apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which.

DESCRIPTION

Figure 1:
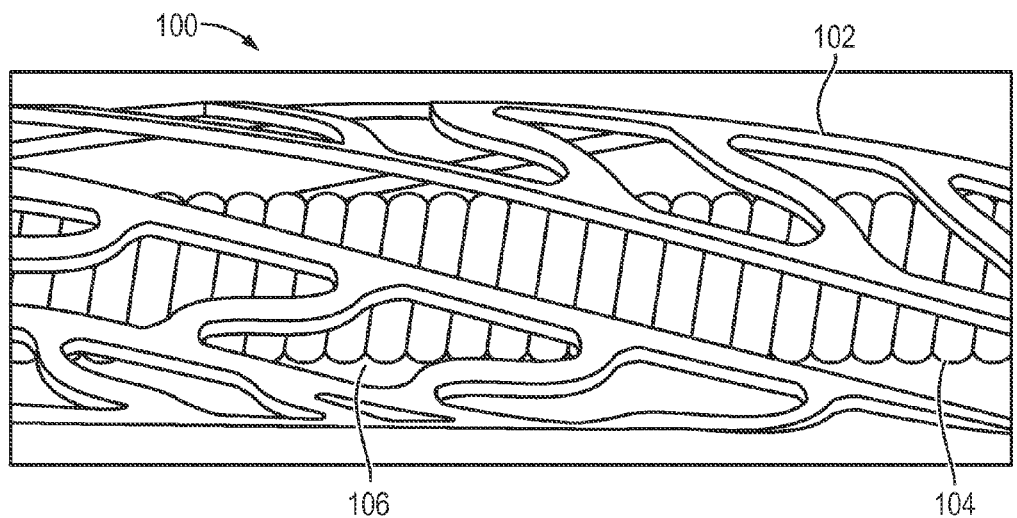
FIG. 1 is a schematic side view of an embolic implant having a coil and a cover component according to one embodiment.
Figure 2:
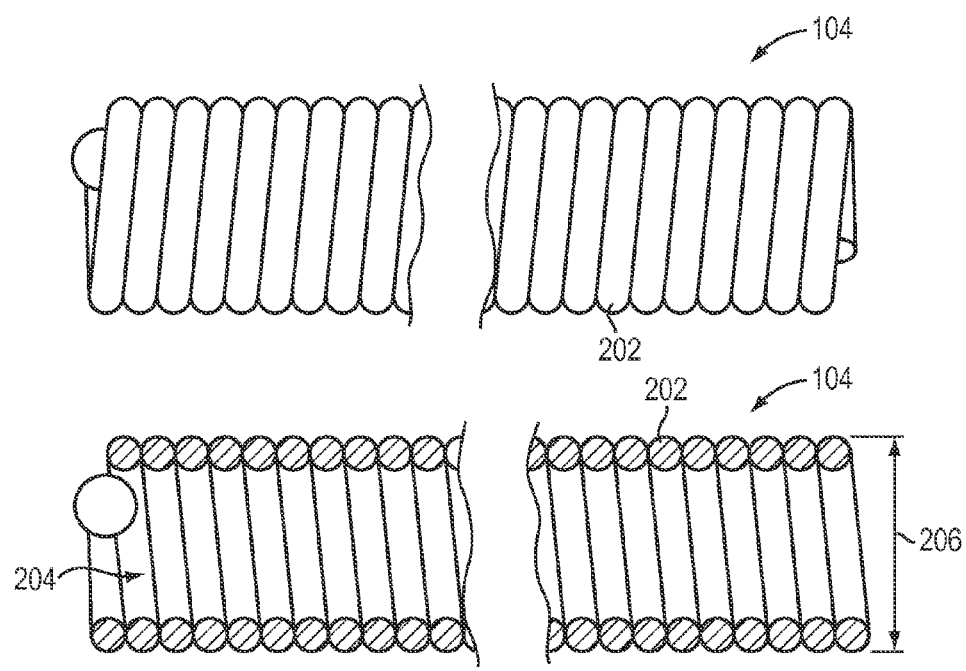
FIG. 2 shows schematic side views, one of which is partially broken away, showing a coil according to one embodiment.
Figure 3:
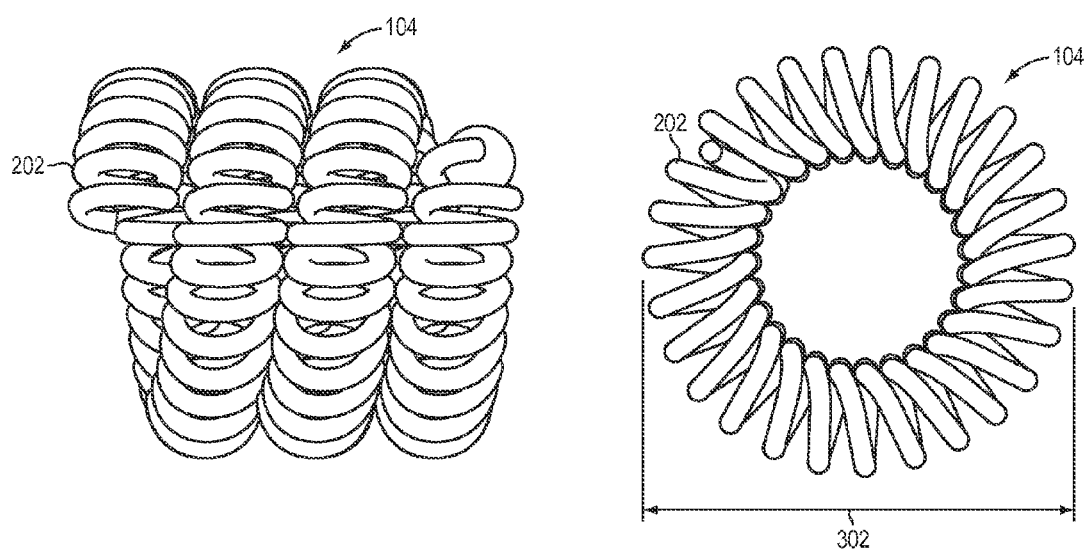
FIG. 3 shows a schematic side view and an end view of a coil wound into a shape having a secondary diameter according to one embodiment.

Embodiments of the present invention are directed to a novel design and manufacturing process for a covered embolic implant 100 that are superior to existing implants and manufacturing processes and that can achieve more effective and predictable outcomes during the treatment of aneurysms. As shown in FIG. 1, in one embodiment, the implant 100 includes a cover component 102 disposed about the exterior of a microcoil 104. In general, the cover 102 and coil 104 may be employed with known bare platinum coil (BPC) based techniques and processes, for example, microcatheter delivery and radiopacity/visualization, and in conjunction certain known accessories. With reference to FIG. 2, the coil 104 may be formed by helically winding a wire 202 and heat setting it into shape such that it forms a lumen 204. The diameter 206 of the lumen 204 is sometimes referred to as the primary diameter. Upon deployment into a vascular disorder, the coil 104 can take a secondary shape (e.g., helical or complex loops) as shown, for example, in FIG. 3. The secondary shape can have a secondary diameter 302. The cover 102 may be compatible with framing, filing, and finishing coils. In certain instances, covered framing coils exhibit better fixation, in their secondary shape, of the secondary diameter 302 upon deployment of the implant 100 into a vascular disorder, which can result in less "tumbling" or "spinning" This results in improved stability of the framing coils, as well as improved overall stability of the implant 100 during deployment of filling and finishing coils.

Figure 4A:
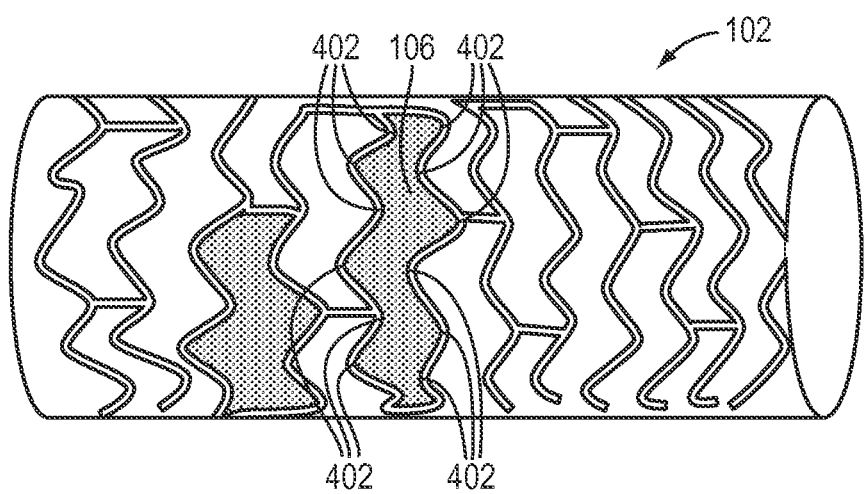
FIG. 4A is a schematic side view showing an example open-cell pattern according to one embodiment.
Figure 4B:
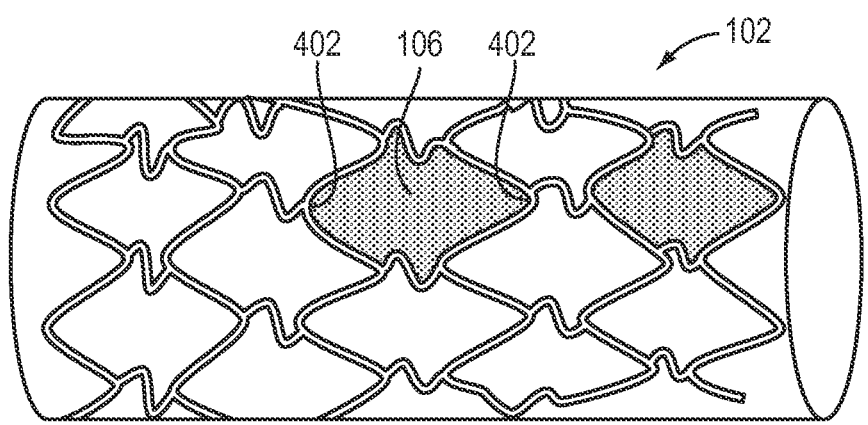
FIG. 4B is a schematic side view showing an example closed-cell pattern according to one embodiment.

As shown in FIG. 1, the cover 102 may include a pattern having pores or cells 106, similar to the pattern found on a medical stent. In some instances, the pattern features open cells 106 as shown in FIG. 4A. In other instances, the pattern features closed cells 106 as shown in FIG. 4B. As used in this disclosure, an open cell refers to a cell having greater than two expansion hinges 402 about which the cell expands in a single dimension at a time. In contrast, as used in this disclosure, a closed cell refers to a cell having two or less expansion hinges 402 about which the cell expands in a single dimension at a time. In still other instances, the pattern features a hybrid design having both open and closed cells. The cover 102 can be formed from either a single strip or multiple strips of material having the pattern (e.g., a through-thickness pattern) cut therein. In such cases, the cover 102 is of unitary construction, which is understood to mean a cover whose cells are formed by the application of a subtractive manufacturing technique to a monolithic piece of material (described in greater detail below). In this way, a cover of unitary construction is different from a cover in which the cells are formed by multiple overlapping fibers or wires as featured in a fibrous braided cover. In some cases, the cover 102 is disposed about the coil 104 in a helical pattern, but may be disposed in other patterns as well.

Figure 5:
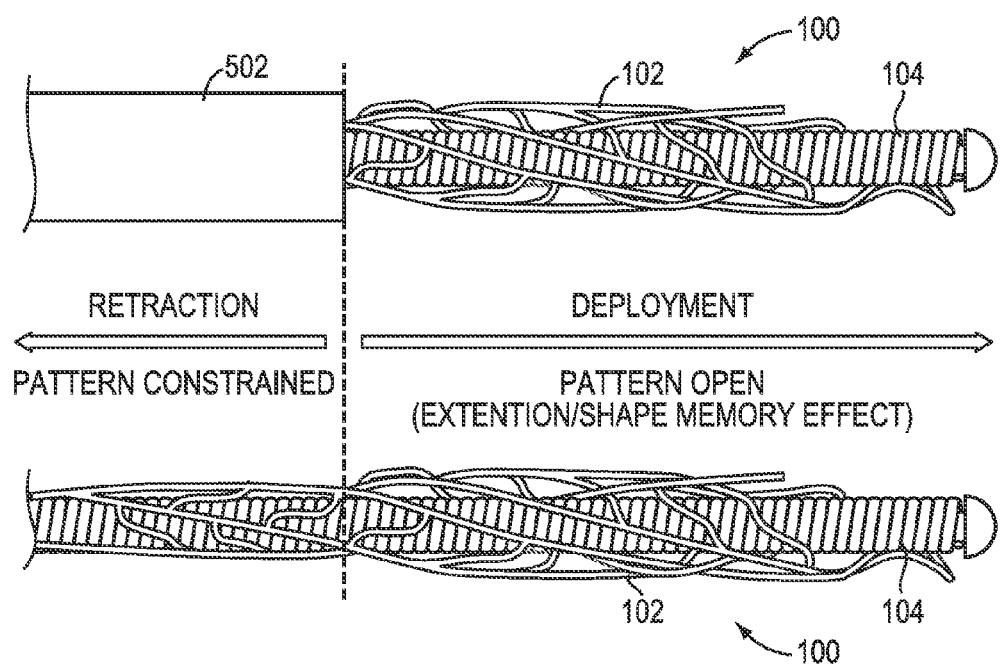
FIG. 5 is a schematic side view showing a cover having a constrained and an expanded configuration according to one embodiment.
Figure 6:
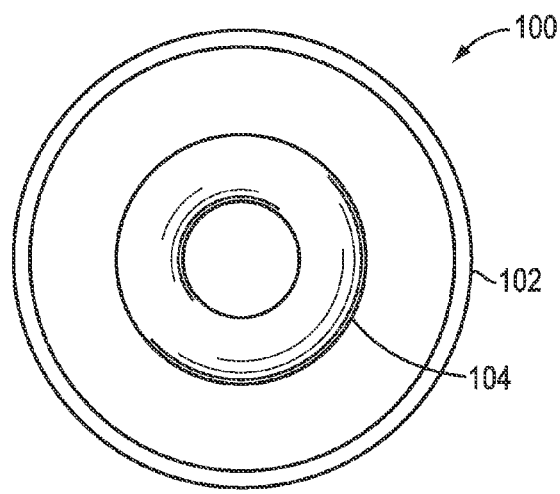
FIG. 6 is a schematic end view of a cover in its expanded configuration disposed about a coil according to one embodiment.
Figure 13:
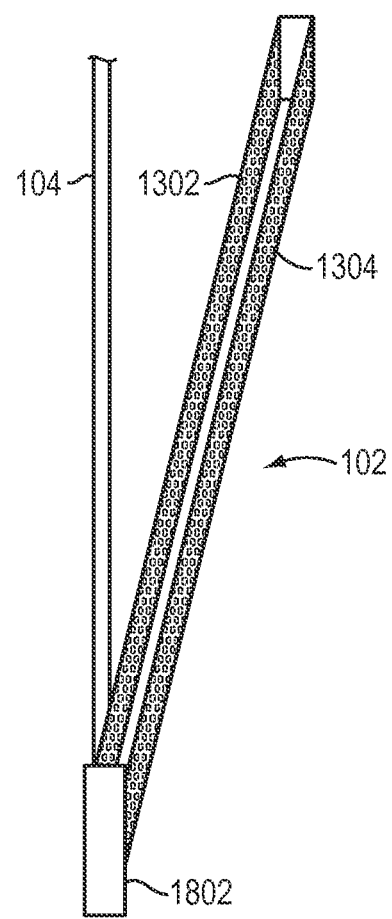
FIG. 13 is a schematic side view showing a cover having two strips of material according to one embodiment.

As shown in FIG. 5, in some embodiments, the cover 102 has a constrained configuration while being delivered to a vascular disorder through a delivery device 502 (e.g., a delivery tube or microcatheter) and an expanded configuration after being deployed out of the delivery device 502 into the vascular disorder. The cover 102 may be concentric with the coil 104 in the constrained configuration during deployment. After deployment, in the expanded configuration, the cover 102 may remain concentric with the coil 104 or become eccentric with the coil 104. In its constrained configuration, the cover 102 may rest against the exterior of the coil 104, but not extend into its lumen 204. In its expanded configuration, with the exception of the contact made at and around the connection portion(s) 1802 (described below, with reference to FIGS. 13, 18, and 19), the cover 102 may be spaced apart from the coil 104, such that in cross-sectional view the cover 102 does not intersect the coil 104. An example of such a cross-sectional view is shown in FIG. 6.

Expansion of the cover 102 may be accomplished through, for example, the through-thickness cut patterns and/or shape memory characteristics of the cover's material. For example, when the cover 102 is in the constrained configuration, the spacing and size of the cells 106 may be reduced (e.g., by forces applied by the delivery device 502), thereby shrinking the cover's cross-sectional profile (e.g., outer diameter). Upon removal of the constraining forces (e.g., upon deployment of the implant 100 into the aneurysm), the spacing and size of the cells 106 may increase (e.g., through the action of the shape memory material), thereby resulting in an expansion of the cover's profile (e.g., outer diameter). In certain instances, the cover 102 includes materials with natural shape memory characteristics (e.g., nitinol, shape memory polymers). In other instances, shape memory characteristics are imparted to the cover's material with compressive and/or tensile surface stress management using mechanical or ion implantation techniques.

In the expanded configuration, the cover may have an outer diameter, profile, and biocompatible blood-contacting surface area in a range from 110% to 200% of those parameters of the coil 104 alone. In some embodiments, the cover 102 can enable the embolic implant 100 to fill a vascular disorder with a significantly greater volume (i.e., packing volume) per unit length of coil 104 than existing devices. In some instances, the packing volume of the implant 100 with a cover 102 in its expanded configuration is between 2 and 7 times as great as the packing volume of the coil 104 without the cover 102. An increased packing volume can help achieve greater effective flow diversion of blood away from the aneurysm through enhanced coverage and blockage of the aneurysm neck.

Figure 7:
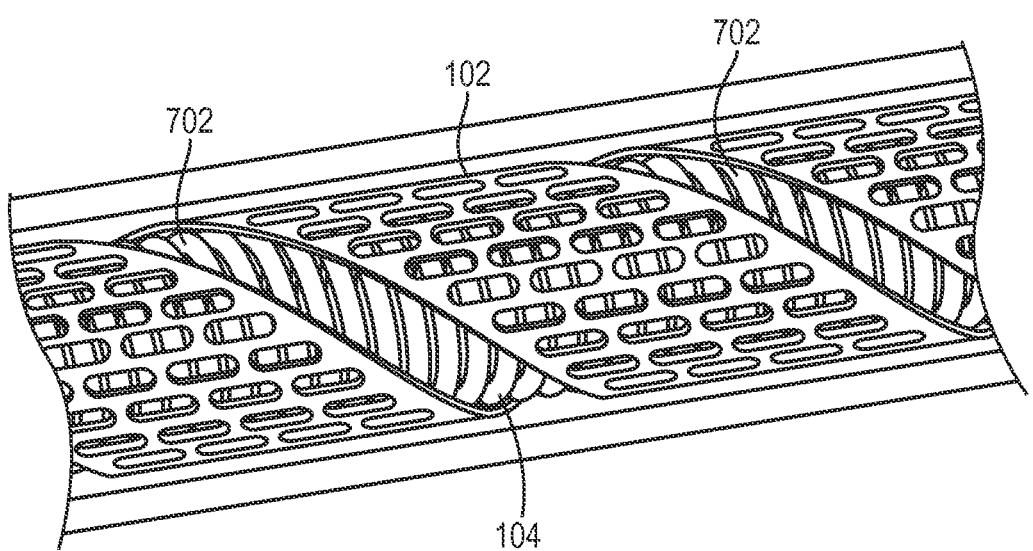
FIG. 7 is a schematic perspective view of a cover in its constrained configuration disposed about a coil according to one embodiment.

In addition, the expanded profile of the cover 102 results in a larger biocompatible blood-contacting surface area, which can improve stasis of blood-flow within the aneurysm sac. Upon expansion, the cover 102 may also cover more surface area of the coil 104 than in its constrained configuration. As FIG. 7 shows, in some embodiments, when the cover 102 is in its constrained configuration, there are gaps 702 in which the cover 102 does not cover the coil 104. In some instances, these gaps 702 are narrowed or closed entirely when the cover 102 enters its expanded configuration, resulting in the cover 102 covering more surface area of the coil 104.

In addition to the cover's increase of the packing volume and biocompatible blood-contacting surface area of the implant 100, it is also softer and more flexible than existing covers because of its unitary construction. Being of unitary construction allows the cells 106 to be designed such that the cover 102 expands an appropriate amount, but not an excessive amount so as to risk rupture of the aneurysm. Such design is not possible with the inherently stiff wire-on-wire design of existing braided covers. More generally, the pattern of the cover 102 can be designed to include cells 106 having shapes, sizes, and/or configurations to achieve desired flow diversion, blood interaction, and/or force/expansion characteristics of the cover 102. The pattern design can also affect cover 102 flexibility. As a result of its unitary construction, the cover 102 also does not exhibit the fretting (e.g., mechanical and/or corrosive wear) characteristic of fiber braided covers.

The cover 102 may also provide a vehicle or platform for the application of multiple treatments and/or therapies including, for example, functionalized and/or bioactive coatings, drug coatings, gene therapies, thrombogenicity control coatings, and surface modifications (e.g., surface texture and/or roughness modifications, ion implantation, and surface charge alterations). At the same time, the cover 102 preserves key coil performance attributes such as, for example, softness and filling capacity.

In operation, the implant 100 may be delivered to the desired site using a microcatheter (e.g., a flexible, small diameter catheter typically, but not necessarily, having an inside diameter between 0.016 inches and 0.021 inches). The microcatheter may be guided to the site through the use of an introducer sheath/guidewire. Guidewires typically comprise long, torqueable proximal wire sections with flexible distal wire sections designed to be visible using fluoroscopy and to be advanced within tortuous vessels to the desired site, thereby allowing the microcatheter to be advanced over the guidewire to access the desired site. Once the site has been accessed with the microcatheter tip, the catheter lumen is cleared by removing the guidewire, and the implant 100 is placed into the proximal open end of the microcatheter and advanced through the microcatheter into the vascular site.

Figure 8:
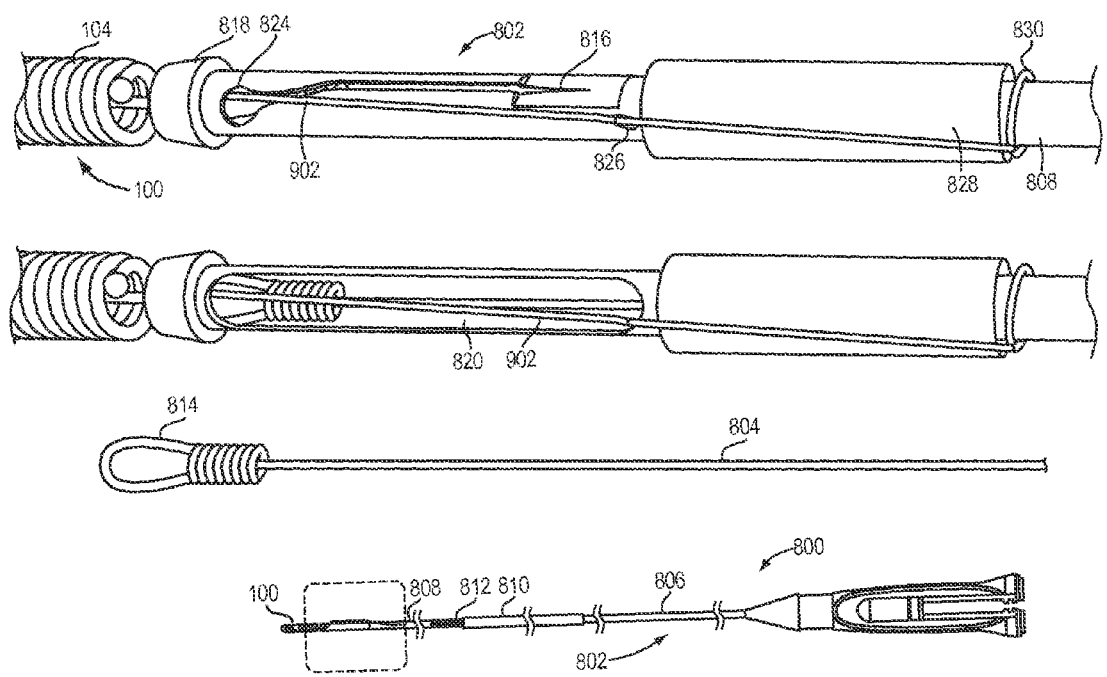
FIG. 8 shows schematic perspective views and a side view of example components of a delivery device according to one embodiment.

In some embodiments, as shown in FIG. 8, the implant 100 may be delivered using a delivery device 800. For simplicity, the cover 102 is not illustrated in FIG. 8, but it will be understood that in embodiments in which the cover 102 is directly attached to the coil 104, the cover 102 may be delivered upon delivery of the coil 104. The implant 100 may be attached to a delivery pusher 802 containing a retractable release wire 804. The delivery pusher 802 may include a proximal shaft 806 made from rigid, metal hypotube to provide good pushability during delivery and stability during detachment of the implant 100; a flexible distal shaft assembly that includes a flexible inner shaft 808 made from a rigid thin-walled polymer tube and flexible outer shaft 810 also made from a rigid thin-walled polymer tube; and an anti-elongation component 812 (e.g., a metallic ribbon/strip). In some instances, the release wire 804 includes a core wire that is, for example, made from 300 series stainless steel, between 35 cm and 75 cm in length, ground on its distal end, and coated on the unground section with polytetrafluoroethylene (PTFE) to reduce friction. In some cases, the core wire is about 0.006 inches in diameter, and ground to about 0.002 inches at the tip. Attached to the wire 804 can be a coil loop 814 created by winding a segment of wire into a short coil (e.g., about 1 mm in diameter) and a short "hook" and soldering these components to the tip of the release wire 804. In some cases, the coil loop 814 can be made from, for example, 300 series stainless steel wire having a diameter of about 0.001 inches.

In some instances, a stationary blade 816 is attached to the distal end of the flexible inner shaft 808. The stationary blade 816 may be made from, for example, 300 series stainless steel and attached using an adhesive. The stationary blade 816 may be attached behind a polymer tip 818 (e.g., pebax-polyether block amide), which may provide an atraumatic interface and help secure the blade 816 to the inner shaft 808. The flexible inner shaft 808 may include a window cutout 820 that allows a detachment suture 902 (described below) to move within the geometry of the blade 816. The window 820 may be, for example, hand cut, machine cut, ground, or laser cut.

Figure 9:
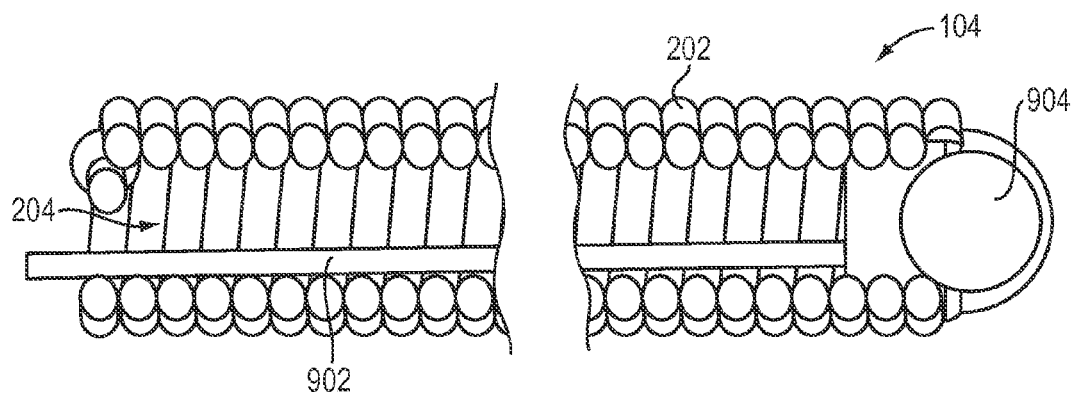
FIG. 9 shows a partially broken away schematic side view of a stretch resistant member attached to a coil according to one embodiment.

With reference to FIG. 9, in some instances, a stretch resistant member 902 (e.g., a polymer suture) may attach to the coil 104 and extend along its lumen 204. In particular, the suture 902 may extend along the lumen 204 from a ball of polymer suture 904 placed (e.g., melted) at a distal end of the coil 104. In some cases, the suture 902 is made of monofilament polypropylene (or, in some cases, of other polymers) having an outer diameter in a range between 0.0005 inches and 0.003 inches. The suture 902 may be configured as a single or multifilament (e.g., N≥2) strand through the lumen 204 of the coil 104. In some instances, the suture 902 can employ strategically placed features on the proximal end of the coil 104 to further aid with containing the working length of the suture 902 through the lumen 204 of the coil 104, which can reduce excessive "pull-out" of the suture 902 during delivery and retraction of the embolic implant 100 through a microcatheter. The suture 902 may be attached to the coil 104 before or after the cover 102 has been attached.

Figure 10:
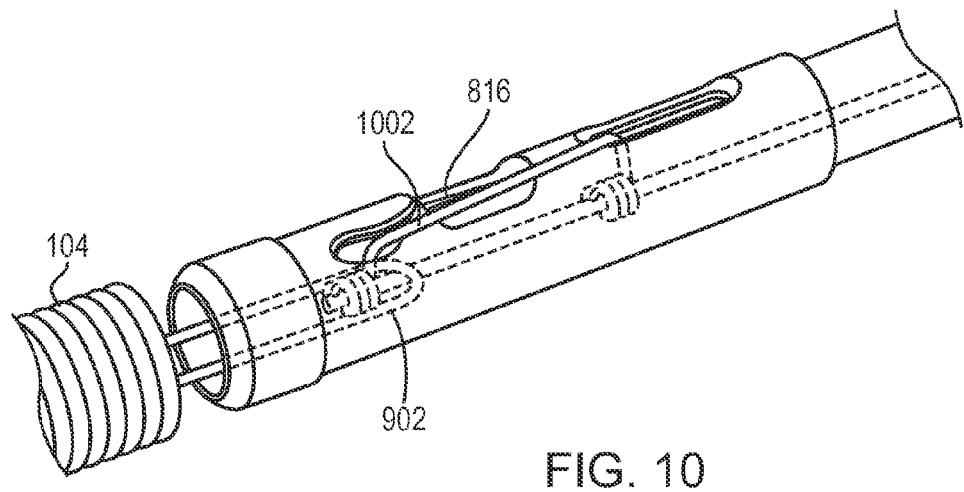
FIG. 10 is a schematic perspective view showing a coil detachment mechanism including a detachment suture according to one embodiment.

As illustrated in FIG. 8, in various embodiments, the suture 902 extends from the coil 104, is threaded through the inside diameter of the tip 818 of the delivery pusher 802, through the coil loop 814, and through a front opening 824 of the attached blade 816, is aligned with a notch 826 in the proximal end of the blade 816, and is attached to the flexible inner shaft 808 by a suture locking tube 828. Additionally, the proximal end of the suture 902 may be tied into a knot 830 around the inner shaft 808 and adhesive may be applied to the knot 830 or the knot 830 may be slightly melted to further secure the suture 902 in position. In another embodiment, as shown for example in FIG. 10, the suture 902 extending from the coil 104 may be configured as a small loop on its proximal end, which is subsequently looped with a second "sacrificial" detachment loop 1002 that is threaded through a series of ports and channels within the stationary blade component 816 and severed upon detachment actuation, thereby releasing the implant 100 into the aneurysm.

Figure 11:
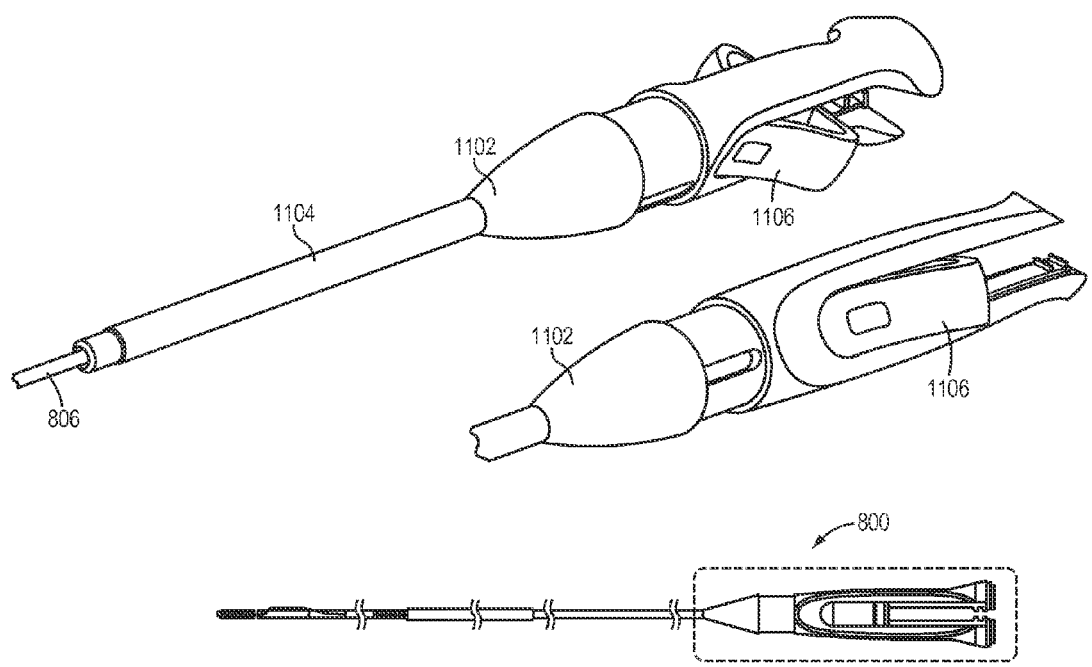
FIG. 11 shows schematic perspective views and a side view of a user-operated handle portion of a delivery device according to one embodiment.

As shown for example in FIG. 11, the proximal shaft 806 may be connected to a handle body 1102 by applying adhesive or employing a press fit. The handle body 1102 may include one or more injection molded parts made from, for example, acrylonitrile butadiene styrene (ABS). There may also be a strain relief 1104 made from, for example, pebax, to help prevent kinking at the junction of the proximal shaft 806 and handle body 1102. The proximal end of the release wire 804 may be secured to a handle slider 1106 by threading the wire 804 through a channel in the slider 1106 and bending the wire 804 to form a mechanical hook bond within the slider 1106. Other attachment techniques (e.g., an adhesive) may also be used to secure these two components together.

The suture 902 may be severed so as to release the embolic implant 100 from the delivery pusher 802 into a vascular disorder. In some instances, this release is accomplished by the refraction of the handle slider 1106 by a user. Since the suture 902 extending from the coil 104 is threaded through the coil loop 814, which is attached to the retractable release wire 804, when the release wire 804 is retracted (by retraction of the handle slider 1106), the coil loop 814 pulls the suture 902 into the blade 816, thereby severing the suture 902 and releasing the implant 100 from the delivery pusher 802 into the aneurysm.

When manufacturing the delivery device 800, the handle body 1102 and handle slider 1106 can be assembled in a locked position, which locks the release wire 804 and coil loop 814 in position relative to the blade 816. These parts may be held in place by, for example, detent features molded into the handle body 1102 and handle slider 1106 mating surfaces.

Figure 12:
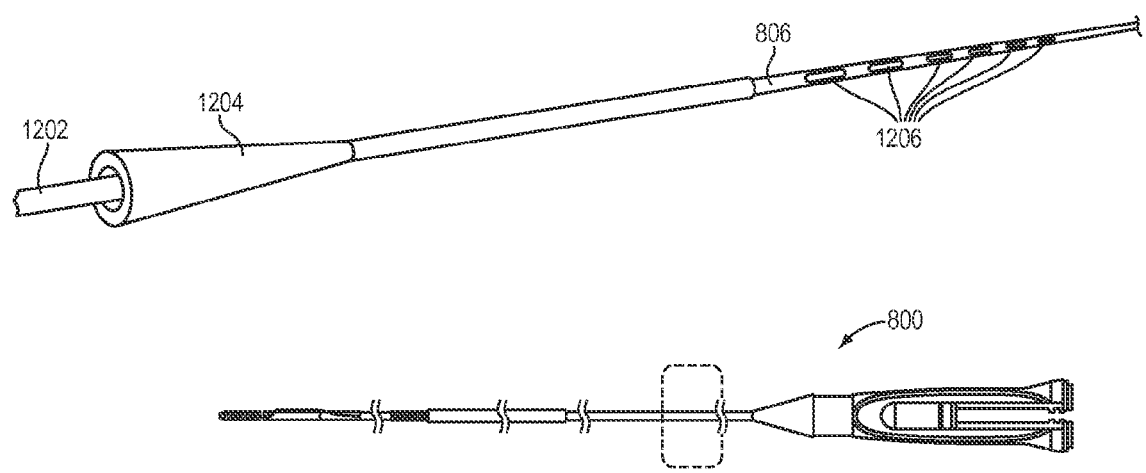
FIG. 12 shows a schematic perspective and side view of additional components of a delivery device according to one embodiment.

In some embodiments, as shown for example in FIG. 12, the delivery device 800 includes an introducer sheath 1202, which protects the embolic implant 100 during sterilization and shipment, and a proximal locking tube 1204, which locks the introducer sheath 1202 in place on the proximal shaft 806. The device 800 may include proximal shaft markings 1206, which can be, for example, laser-etched into the hypotube. These markings 1206 may designate to a user, during introduction of the implant 100 into the microcatheter, the position of the implant 100 relative to the microcatheter tip, thereby saving fluoroscopy time and reducing unnecessary x-ray radiation.

Further embodiments and description of the delivery device 800, including the attachment of the suture 902 to the coil 104, may be found in U.S. patent application Ser. No. 14/196,244, which is incorporated herein by reference in its entirety.

With reference back to FIG. 1, the cover 102 may be manufactured from a flat foil (e.g., a sheet) made from a number of biocompatible, MRI-safe materials, for example metals, absorbable and non-absorbable polymers, ceramics, and composites. Exemplary metals include nitinol, tantalum and alloys, tungsten and alloys, platinum/tungsten alloy, platinum, platinum iridium, cobalt chrome alloys, magnesium, iron, and stainless steel. In some instances, the foil has a thickness in a range from 5 to 250 microns. Manufacturing the cover 102 from a flat sheet may reduce component cost, ensure raw material availability, and increase component manufacture repeatability and scalability. Patterns of cells 106 may be cut into the foil using known cutting techniques including, for example, laser, mechanical, wet chemical, mask or maskless electrochemical, etching/milling, photochemical (e.g., photolithographic) etching/milling, and photoresist/reactive ion or inert gas etch (RIE). The cells 106 may be formed using other subtractive manufacturing techniques as well. Photochemical and photoelectrochemical machining is a well-established, mature technology that is cost-effective, repeatable, scalable, and capable of producing miniature features with high quality resolution. Given that an implant 100 may require a cover 102 having a length of 50 cm or more, mass exposure and patterning techniques that have been proven possible with photochemical (and electrochemical) machining methods may be effective. In other instances, through-mask cutting and/or ablation using, for example, an excimer laser can be used as well.

As stated above, in some embodiments, the cover 102 includes multiple separate strips of patterned material, which can be joined at a connection portion 1802. For example, the cover 102 may include two patterned strips that are helically wound about the coil 104. An example of this configuration can be seen in FIG. 13, which shows the cover 102 having two strips of material 1302, 1304 that may be helically wound about coil 104.

Figure 14:
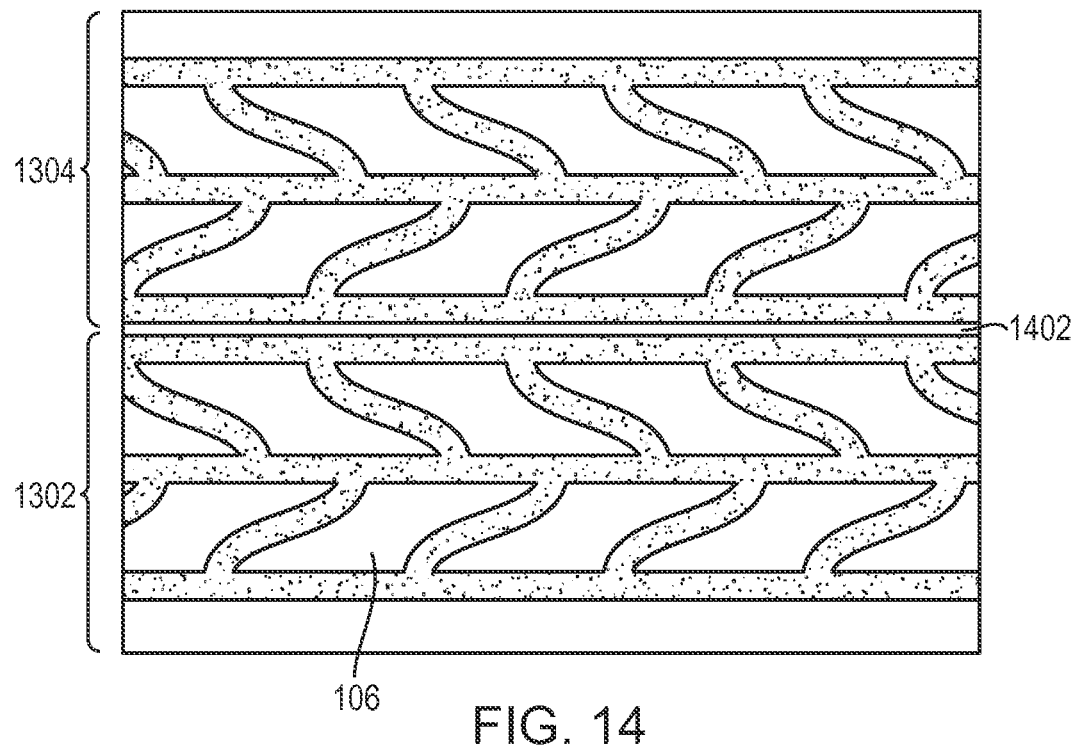
FIG. 14 is a schematic top view of a monolithic foil from which multiple portions of a cover can be manufactured according to one embodiment.

FIG. 14 shows an example foil that has been cut with a pattern of cells 106. In this example, the pattern was cut into a single monolithic piece, which was then separated by cut 1402 to create two separate strips 1302, 1304. In other cases, no cut is made in the monolithic piece and the cover 102 includes only a single strip of material. In still other cases, multiple cuts are made in the monolithic piece and the cover 102 includes more than two strips of material. In other embodiments, the coil 104 can be covered with two or more covers 102, each manufactured from a separate monolithic piece.

Figure 15:
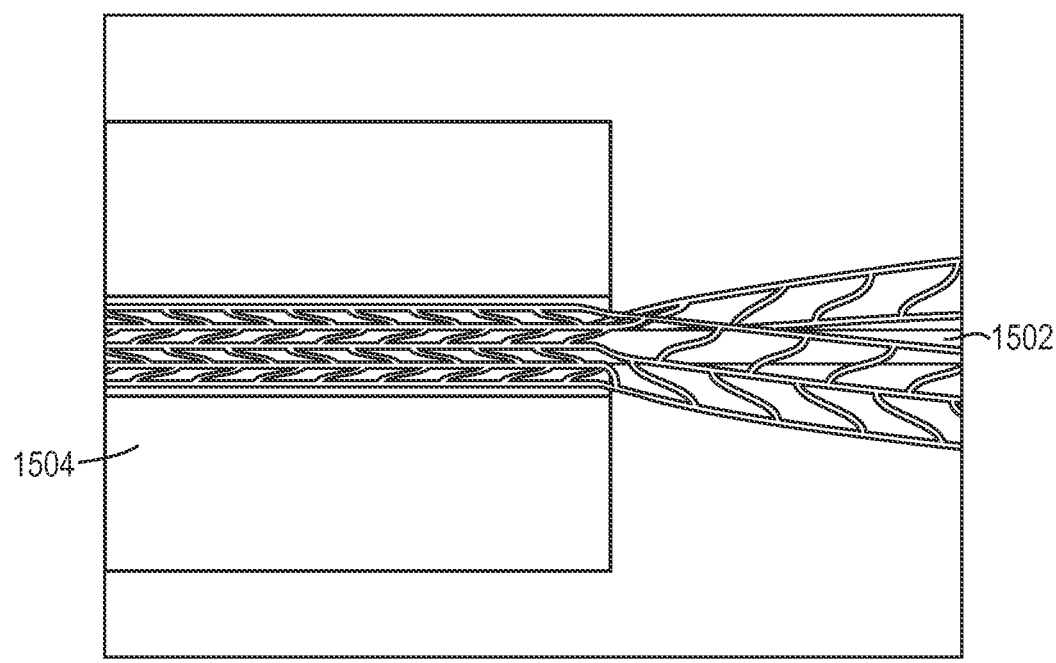
FIG. 15 is a schematic side view showing an example technique for forming a flat foil into a tubular geometry according to one embodiment.
Figure 16:
FIG. 16 is a schematic side view of an embolic implant held with a holding tube according to one embodiment.

In embodiments in which the pattern is cut into a flat foil, the foil may be reverted into a tubular geometry in order to be disposed over the coil 104. In some instances, the foil is reverted into a tubular or cylindrical geometry prior to being placed over the coil 104. As shown, for example, in FIG. 15, this process may include forming the patterned foil into a desired tubular geometry about an inner support mandrel 1502 within a rigid tube 1504, which holds the foil in place. The foil may then be heat set such that it retains its tubular geometry. Once heat set and removed from the support mandrel, the foil (now in the shape of cover 102) can be simultaneously pulled over the coil 104 and into a holding tube 1602 such that it is in its constrained configuration (e.g., as shown in FIG. 16). In other instances, the separate step of reverting the foil into a tubular geometry using the inner support mandrel 1502 and rigid tube 1504 may be bypassed, and the foil may be reverted to its tubular formation at the same time that it is placed in the holding tube 1602 over the coil 104. In such instances, the foil may be heat set into place while within the holding tube 1602. In other embodiments, the need to revert the foil into a tubular geometry can be bypassed altogether by cutting the pattern into a material already having a tubular geometry rather than a flat foil.

Figure 17:
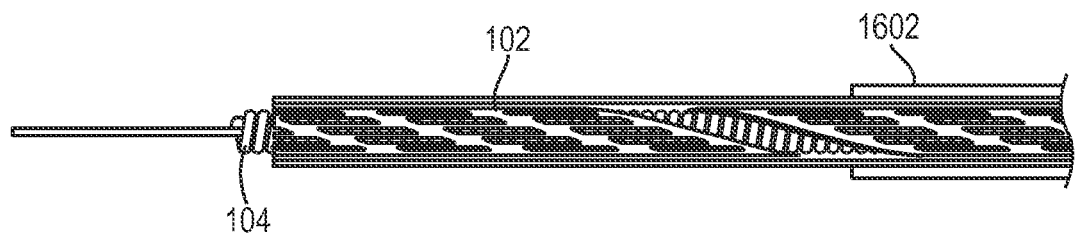
FIG. 17 is a schematic side view of a cover/coil attachment site according to one embodiment.
Figure 18:
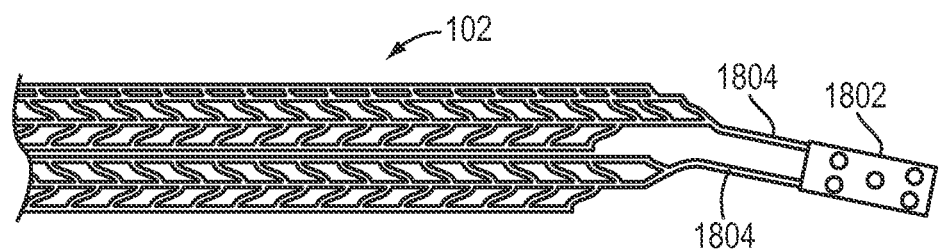
FIG. 18 is a schematic top view of a flat foil including a connection portion according to one embodiment.
Figure 19:
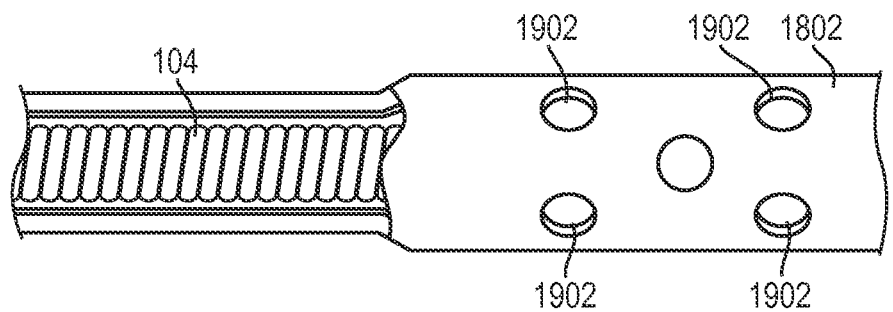
FIG. 19 is a schematic side view of a connection portion in operation according to one embodiment.

Regardless of how the cover 102 is formed into its tubular geometry, it may be attached to the coil 104 in various ways. In some instances, after the cover 102 and coil 104 are simultaneously pulled into the holding tube 1602, the distal and/or proximal end of the implant 100 may be exposed and various attachment techniques may be employed (e.g., as shown in FIG. 17). A non-exclusive list of such attachment techniques includes: mechanical/interference fit, laser welding, spot welding, resistance welding, diffusion bonding, soldering, brazing and/or application of Class III approved medical adhesives or continual coatings. In some instances, attachment may occur via a connection portion 1802, an example of which is shown in FIGS. 18 and 19. As shown in FIG. 18, in some cases, the connection portion 1802 may be manufactured from the same monolithic piece of material as the patterned portions. Arms 1804 may also be manufactured to extend from the connection portion 1802 to the patterned portions. In other cases, the connection portion 1802 is manufactured separately and attached to the patterned portions using known techniques. As shown in FIG. 19, the connection portion 1802 can enable attachment to the coil 104 by being wrapped around the coil 104. In various instances, the connection portion 1802 may include through-thickness features 1902 (e.g., holes or patterns) to facilitate the connection. The connection portion 1802 may be designed to have an inner diameter such that an interference fit with the outer diameter of coil 104 is possible. In instances in which the connection portion 1802 is connected directly to the coil 104, the coil 104 and cover 102 can both be released into a vascular disorder upon release of the coil 104 from the delivery pusher 802 (e.g., as described above with reference to FIGS. 8 through 12).

Following attachment of the cover 102 to the coil 104, the embolic implant 100 may be placed into a second tube and then attached to the delivery device 800 (e.g., onto delivery pusher 802). In some instances, the cover 102 is connected only at one of either the proximal or distal end of the coil 104 while remaining unrestrained at the opposite end. In such instances, when the cover 102 expands and/or contracts, it may shorten and/or lengthen at its unrestrained portion, depending on the through-thickness cut pattern of the cover 102. In other instances, the cover 102 is connected to the coil 104 at both the proximal and distal ends of the coil 104. In such instances, when the cover 102 expands and/or contracts, the body of the cover (i.e., portion between the connected ends) may shorten and/or lengthen, depending on the through-thickness cut pattern of the cover 102. In some such instances, the arms 804 may lengthen and/or shorten. The cover's longitudinal forgiveness, which allows it to lengthen and/or shorten, may be enabled by the through-thickness cut pattern. In certain embodiments, regardless of whether the cover 102 is connected at one or both ends of the coil 104, the cover 102 is designed (e.g., a particular through-thickness pattern is implemented) such that when the cover 102 expands and/or contracts it exhibits no, or minimal, shortening and/or lengthening, and in some cases may maintain a length the same as, or close to, that of the coil 104.

Having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. An implant adapted for use in treating a vascular disorder, the implant comprising:
   an embolic coil forming a lumen; and
   a cover of unitary construction helically wound about an exterior of the embolic coil, wherein (i) the cover does not extend into the lumen, (ii) the cover is expandable such that the cover covers the embolic coil in a constrained configuration during delivery of the implant to the vascular disorder and assumes an expanded configuration when the implant is placed within the vascular disorder, and (iii) the cover covers more surface area of the embolic coil in the expanded configuration than in the constrained configuration.

2. The implant of claim 1, wherein the embolic coil comprises a bare platinum coil.

3. The implant of claim 1, wherein the cover is spaced apart from the embolic coil along at least a portion of the embolic coil when the cover is in the expanded configuration.

4. The implant of claim 1, wherein, in the expanded configuration of the cover, the implant comprises a biocompatible blood-contacting surface area between 110% and 200% of the embolic coil alone.

5. The implant of claim 1, wherein the cover comprises a shape memory material.

6. The implant of claim 1, wherein the cover comprises a pattern.

7. The implant of claim 6, wherein the pattern comprises a through-thickness cut pattern.

8. The implant of claim 6, wherein the pattern comprises cells comprising at least one of closed cells, open cells, hybrid cells, and combinations thereof.

9. The implant of claim 8, wherein the cells are sized as a function of at least one of flow diversion, blood interaction, and expansion characteristics of the cover.

10. The implant of claim 8, wherein the cells comprise a constrained configuration and an expanded configuration.

11. The implant of claim 1, wherein the cover comprises at least one of a functionalized bioactive coating, a drug coating, a gene therapy coating, a thrombogenicity control coating, and surface modifications.

12. The implant of claim 11, wherein the surface modifications are selected from the group consisting of surface texture alterations, surface roughness alterations, ion implantations, and surface charge alterations.

13. The implant of claim 1, wherein the cover and the embolic coil are concentric.

14. The implant of claim 1, wherein the cover and the embolic coil are eccentric.

15. The implant of claim 1, wherein the implant comprises a packing volume in a range from 2 to 7 times a packing volume of the embolic coil alone.

16. The implant of claim 1, wherein the embolic coil is selected from the group consisting of a framing coil, a filling coil, and a finishing coil.

17. The implant of claim 1, wherein the cover comprises a biocompatible MRI-safe material.

18. The implant of claim 1, wherein the cover comprises a length of up to 50 centimeters.

19. The implant of claim 1, further comprising a second cover of unitary construction disposed about the exterior of the embolic coil, wherein the second cover does not extend into the lumen.

20. A method of delivering an implant to a vascular disorder, the method comprising the steps of:
   advancing the implant, coupled to a delivery pusher, in proximity to the vascular disorder, the implant comprising:
      (i) an embolic coil forming a lumen; and
      (ii) a cover of unitary construction helically wound about an exterior of the embolic coil in a constrained configuration, wherein (a) the cover does not extend into the lumen, (b) the cover is expandable such that the cover covers the embolic coil in the constrained configuration during delivery of the implant to the vascular disorder and assumes an expanded configuration when the implant is placed within the vascular disorder, and (c) the cover covers more surface area of the embolic coil in the expanded configuration than in the constrained configuration; and
   releasing the implant from the delivery pusher and into the vascular disorder, whereby the cover expands into the expanded configuration.

21. The method of claim 20, wherein the vascular disorder comprises a cerebral aneurysm.

22. The method of claim 20, wherein, in the expanded configuration of the cover, the implant comprises a biocompatible blood-contacting surface area between 110% and 200% of the embolic coil alone.

23. The method of claim 20, wherein the cover is spaced apart from the embolic coil along at least a portion of the embolic coil when the cover is in the expanded configuration.

24. The method of claim 20, wherein the cover comprises a shape memory material.

25. The method of claim 20, wherein the cover comprises a through-thickness cut pattern.

26. A method of manufacturing an implant for use in treating a vascular disorder, the method comprising the steps of:
    obtaining an embolic coil forming a lumen;
    forming a cover of unitary construction by creating a pattern in a sheet of unitary construction using a subtractive manufacturing technique; and
    helically winding the cover about an exterior of the embolic coil, such that the cover does not extend into the lumen formed by the embolic coil, wherein (i) the cover is expandable such that the cover covers the embolic coil in a constrained configuration during delivery of the implant to the vascular disorder and assumes an expanded configuration when the implant is placed within the vascular disorder and (ii) the cover covers more surface area of the embolic coil in the expanded configuration than in the constrained configuration.

27. The method of claim 26, wherein the sheet comprises a metallic foil.

28. The method of claim 27, wherein the metallic foil comprises a material selected from the group consisting of nitinol, tantalum, tungsten, platinum, platinum iridium, cobalt chrome, magnesium, iron, stainless steel, and combinations and alloys thereof.

29. The method of claim 26, wherein the sheet comprises a thickness in a range from about 5 microns to about 250 microns.

30. The method of claim 26, wherein the subtractive manufacturing technique is selected from the group consisting of a laser technique, a mechanical technique, a wet chemical technique, an electrochemical masking technique, a maskless electrochemical technique, etching, milling, photochemical machining, and photoelectrochemical machining.

31. The method of claim 26, wherein the step of helically winding the cover about the exterior of the embolic coil comprises shaping the cover into a tubular geometry and placing the cover over the embolic coil.

32. The method of claim 31, wherein the step of shaping the cover into the tubular geometry comprises heat setting.

33. The method of claim 26 further comprising:
    disposing the cover and the embolic coil in a holding tube that maintains the cover in the constrained configuration about the exterior of the embolic coil;
    attaching the cover to the embolic coil at at least one end; and
    pushing the attached cover and embolic coil into a second tube that maintains the constrained configuration of the cover.

34. The method of claim 33, wherein the step of attaching the cover to the embolic coil comprises using an attachment technique selected from the group consisting of laser welding, resistance welding, applying a medical adhesive, applying continual coatings, and employing a mechanical interference fit.

35. The method of claim 33, further comprising attaching the second tube to a delivery pusher.

* * * * *